(12) United States Patent
Mujica-Fernaud et al.

(10) Patent No.: US 7,378,421 B2
(45) Date of Patent: *May 27, 2008

(54) CHROMENONE DERIVATIVES

(75) Inventors: Teresa Mujica-Fernaud, Darmstadt (DE); Herwig Buchholz, Frankfurt (DE); Wilfried Rautenberg, Reinheim (DE); Christian Sirrenberg, Darmstadt (DE)

(73) Assignee: Merck Patent Gesellschaft Mit Beschrankter Haftung, Darmstadt (DE)

( * ) Notice: Subject to any disclaimer, the term of this patent is extended or adjusted under 35 U.S.C. 154(b) by 535 days.

This patent is subject to a terminal disclaimer.

(21) Appl. No.: 10/833,159

(22) Filed: Apr. 28, 2004

(65) Prior Publication Data

US 2004/0220182 A1 Nov. 4, 2004

(30) Foreign Application Priority Data

Apr. 30, 2003 (DE) ............................ 103 19 552
Aug. 5, 2003 (DE) ............................ 103 35 782

(51) Int. Cl.
*A61K 31/4965* (2006.01)
*C07D 405/06* (2006.01)

(52) U.S. Cl. ........................ 514/254.11; 514/227.5; 514/232.5; 514/320; 514/365; 514/374; 514/397; 514/422; 544/242; 544/406; 546/135; 546/146; 546/283.1; 548/146; 548/159; 548/215; 548/250; 548/255; 548/262.2; 548/311.4

(58) Field of Classification Search ............... 544/406, 544/242; 548/311.4, 159, 146, 215, 250, 548/255, 262.2; 546/283.1, 135, 146; 514/227.5, 514/232.5, 254.11, 320, 365, 374, 394, 422
See application file for complete search history.

(56) References Cited

U.S. PATENT DOCUMENTS 6,939,859 B1 * 9/2005 Murase et al. ............... 514/27

FOREIGN PATENT DOCUMENTS

JP 7191431 7/1995

OTHER PUBLICATIONS

Hadjeri et al, Modulation of P-Glycoprotein-Mediated Multidrug Resistance by Flavonoid Derivatives and Analogues, J. Med. Chem. 2003, 46, 2125-2131.*
Hosseinimehr et al, Radioprotective Effects of 2-Imino-3-[(chromone-2-yl)carbonyl]thiazolidines against Irradiation in Mice, J. Radiat. Res., 43, 293-300 (2002).*
West, Anthony R., Solid State Chemistry and its Applications, Wiley, New York, 1988, pp. 358 & 365.*
Wermuth "The practice of medicinal chemiistry" p. 203=208 (1996).*
Braga et al. "Making crystals . . . " Chem. Commun. p. 3635-3645 (2005).*
Patani et al. "Bioisosterism: a rational . . . " Chem. Rev. p. 3147, 3158 (1996).*
Abstract of Silver Halide Photographic Sensitive Material: Toda Yuzo et al. Jul. 28, 1995.

* cited by examiner

*Primary Examiner*—Celia Chang
(74) *Attorney, Agent, or Firm*—Millen, White, Zelano & Branigan, P.C.

(57) ABSTRACT

Novel compounds of the formula I

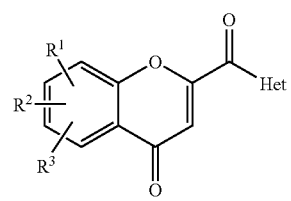

in which
$R^1$, $R^2$, $R^3$ and Het are as defined herein, which are inhibitors of tyrosine kinases and/or Raf kinases and can be employed for the treatment of tumours, for neuroprotection and for protection of the stress proteins of the skin.

8 Claims, No Drawings

CHROMENONE DERIVATIVES

This application claims priority to Germany Application No. 103 19 552.1 filed Apr. 30, 2003 and Germany Application No. 103 35 782.3 filed Aug. 5, 2003.

BACKGROUND OF THE INVENTION

The present invention, in one aspect, relates to compounds in which the inhibition, regulation and/or modulation of kinase signal transduction, in particular tyrosine kinase and Raf kinase signal transduction, plays a role, furthermore to pharmaceutical compositions which comprise these compounds, and to the use of the compounds for the treatment of tyrosine kinase-induced diseases.

In other aspects, the present invention relates to compounds which inhibit, regulate and/or modulate tyrosine kinase signal transduction, to compositions which comprise these compounds, and to methods for the use thereof for the treatment of tyrosine kinase-induced diseases and conditions, such as cancer, tumour growth, arteriosclerosis, age-related macular degeneration, diabetic retinopathy, inflammatory diseases and the like, in mammals.

Tyrosine kinases are a class of enzymes which catalyse the transfer of the terminal phosphate of adenosine triphosphate to tyrosine residues in protein substrates. Tyrosine kinases, through substrate phosphorylation, play a crucial role in signal transduction for a number of cellular functions. Although the precise mechanisms of signal transduction are still unclear, tyrosine kinases have been shown to be important contributing factors in cell proliferation, carcinogenesis and cell differentiation.

Tyrosine kinases can be categorised as receptor-type tyrosine kinases or non-receptor-type tyrosine kinases. Receptor-type tyrosine kinases have an extracellular portion, a transmembrane portion and an intracellular portion, while non-receptor-type tyrosine kinases are exclusively intracellular.

Receptor-type tyrosine kinases contain a multiplicity of transmembrane receptors with different biological activity. Thus, about 20 different subfamilies of receptor-type tyrosine kinases have been identified. One tyrosine kinase subfamily, known as the HER subfamily, consists of EGFR, HER2, HER3 and HER4. Ligands from this subfamily of receptors include epithelial growth factor, TGF-α, amphiregulin, HB-EGF, betacellulin and heregulin. Another subfamily of these receptor-type tyrosine kinases is the insulin subfamily, which includes INS-R, IGF-IR and IR-R. The PDGF subfamily includes the PDGF-α and -β receptors, CSFIR, c-kit and FLK-II. In addition, there is the FLK family, which consists of the kinase insert domain receptor (KDR), foetal liver kinase-1 (FLK-1), foetal liver kinase-4 (FLK-4) and fms tyrosine kinase-1 (flt-1). The PDGF and FLK families are usually discussed together due to the similarities between the two groups. For a detailed discussion of receptor-type tyrosine kinases, see Plowman et al., DN & P 7(6):334-339, 1994, which is hereby incorporated by way of reference.

Non-receptor-type tyrosine kinases likewise contain a multiplicity of subfamilies, including Src, Frk, Btk, Csk, Abl, Zap70, Fes/Fps, Fak, Jak, Ack and LIMK. Each of these subfamilies is further sub-divided into different receptors. For example, the Src subfamily is one of the largest subfamilies. It includes Src, Yes, Fyn, Lyn, Lck, Blk, Hck, Fgr and Yrk. The Src subfamily of enzymes has been linked to oncogenesis. For a more detailed discussion of non-receptor-type tyrosine kinases, see Bolen Oncogene, 8:2025-2031 (1993), which is hereby incorporated by way of reference. Both receptor-type tyrosine kinases and non-receptor-type tyrosine kinases are involved in cellular signalling pathways leading to numerous pathogenic conditions, including cancer, psoriasis and hyperimmune responses.

Various receptor-type tyrosine kinases, and the growth factors binding to them, play a role in angiogenesis, although some may promote angiogenesis indirectly (Mustonen and Alitalo, J. Cell Biol. 129:895-898, 1995). One of these receptor-type tyrosine kinases is foetal liver kinase 1, also referred to as FLK-1. The human analogue of FLK-1 is the kinase insert domain-containing receptor KDR, which is also known as vascular endothelial cell growth factor receptor 2 or VEGFR-2, since it binds VEGF with high affinity. Finally, the murine version of this receptor has also been called NYK (Oelrichs et al., Oncogene 8(1):11-15,1993). VEGF and KDR are a ligand-receptor pair which plays a vital role in the proliferation of vascular endothelial cells and the formation and sprouting of blood vessels, referred to as vasculogenesis and angiogenesis respectively.

Angiogenesis is characterised by excessive activity of vascular endothelial growth factor (VEGF). VEGF contains a family of ligands (Klagsburn and D'Amore, Cytokine & Growth Factor Reviews 7:259-270,1996). VEGF binds the high affinity membrane-spanning tyrosine kinase receptor KDR and the related fms tyrosine kinase-1, also known as Flt-1 or vascular endothelial cell growth factor receptor 1 (VEGFR-1). Cell culture and gene knockout experiments indicate that each receptor contributes to different aspects of angiogenesis. KDR mediates the mitogenic function of VEGF, whereas Flt-1 appears to modulate non-mitogenic functions, such as those associated with cellular adhesion. Inhibiting KDR thus modulates the level of mitogenic VEGF activity. In fact, tumour growth has been shown to be susceptible to the antiangiogenic effects of VEGF receptor antagonists (Kim et al., Nature 362, pp. 841-844, 1993).

Solid tumours can therefore be treated with tyrosine inhibitors since these tumours depend on angiogenesis for the formation of the blood vessels that are necessary to support their growth. These solid tumours include monocytic leukaemia, carcinomas of the brain, urogenital tract, lymphatic system, stomach, larynx and lung, including lung adenocarcinoma and small cell lung carcinoma. Further examples include carcinomas in which overexpression or activation of Raf-activating oncogenes (for example, K-ras, erb-B) is observed. Such carcinomas include pancreatic and breast carcinoma. Inhibitors of these tyrosine kinases are therefore suitable for the prevention and treatment of proliferative diseases caused by these enzymes.

The angiogenic activity of VEGF is not limited to tumours. VEGF accounts for the angiogenic activity produced in or near the retina in diabetic retinopathy. This vascular growth in the retina leads to visual degeneration culminating in blindness. Ocular VEGF mRNA and protein levels are elevated by conditions such as retinal vein occlusion in primates and decreased $pO_2$ levels in mice that lead to neovascularisation. Intraocular injections of anti-VEGF monoclonal antibodies or VEGF receptor immunofusions inhibit ocular neovascularisation in both primate and rodent models. Irrespective of the cause of induction of VEGF in human diabetic retinopathy, inhibition of ocular VEGF is suitable for treating this disease.

Expression of VEGF is also significantly increased in hypoxic regions of animal and human tumours adjacent to areas of necrosis. In addition, VEGF is upregulated by the expression of the oncogenes Ras, Raf, Src and mutant p53 (all of which are relevant in combating cancer). Anti-VEGF monoclonal antibodies inhibit the growth of human tumours in nude mice. Although the same tumour cells continue to express VEGF in culture, the antibodies do not diminish their mitotic rate. Thus, tumour-derived VEGF does not function as an autocrine mitogenic factor. VEGF therefore contributes to tumour growth in vivo by promoting angiogenesis through its paracrine vascular endothelial cell chemotactic and mitogenic activities. These monoclonal antibodies also inhibit the growth of typically less well vascularised human colon carcinomas in athymic mice and decrease the number of tumours arising from inoculated cells.

The expression of a VEGF-binding construct of Flk-1, Flt-1, the mouse KDR receptor homologue truncated to eliminate the cytoplasmic tyrosine kinase domains but retaining a membrane anchor, in viruses virtually stops the growth of a transplantable glioblastoma in mice, presumably by the dominant negative mechanism of heterodimer formation with membrane-spanning endothelial cell VEGF receptors.

Embryonic stem cells, which normally grow as solid tumours in nude mice, do not produce detectable tumours if both VEGF alleles are knocked out. Taken together, these data indicate the role of VEGF in the growth of solid tumours. Inhibition of KDR or Flt-1 is involved in pathological angiogenesis, and these receptors are suitable for the treatment of diseases in which angiogenesis is part of the overall pathology, for example inflammation, diabetic retinal vascularisation, as well as various forms of cancer, since tumour growth is known to be dependent on angiogenesis (Weidner et al., N. Engl. J. Med., 324, pp. 1-8,1991).

The present invention furthermore relates to the compounds as inhibitors of Raf kinases.

Protein phosphorylation is a fundamental process for the regulation of cellular functions. The coordinated action of both protein kinases and phosphatases controls the degrees of phosphorylation and, hence, the activity of specific target proteins. One of the predominant roles of protein phosphorylation is in signal transduction, where extracellular signals are amplified and propagated by a cascade of protein phosphorylation and dephosphorylation events, for example in the $p21^{ras}$/Raf pathway.

The $p21^{ras}$ gene was discovered as an oncogene of the Harvey (H-Ras) and Kirsten (K-Ras) rat sarcoma viruses. In humans, characteristic mutations in the cellular Ras gene (c-Ras) have been associated with many different types of cancer. These mutant alleles, which render Ras constitutively active, have been shown to transform cells, such as, for example, the murine cell line NIH 3T3, in culture.

The $p21^{ras}$ oncogene is a major contributor to the development and progression of human solid carcinomas and is mutated in 30% of all human carcinomas (Bolton et al. (1994) Ann. Rep. Med. Chem., 29, 165-74; Bos. (1989) Cancer Res., 49, 4682-9). In its normal, unmutated form, the Ras protein is a key element of the signal transduction cascade directed by growth factor receptors in almost all tissues (Avruch et al. (1994) Trends Biochem. Sci., 19, 279-83).

Biochemically, Ras is a guanine nucleotide binding protein, and cycling between a GTP-bound activated and a GDP-bound resting form is strictly controlled by Ras endogenous GTPase activity and other regulatory proteins. The Ras gene product binds to guanine triphosphate (GTP) and guanine diphosphate (GDP) and hydrolyses GTP to GDP. Ras is active in the GTP-bound state. In the Ras mutants in cancer cells, the endogenous GTPase activity is reduced and the protein consequently transmits constitutive growth signals to downstream effectors, such as, for example, the enzyme Raf kinase. This leads to the cancerous growth of the cells which carry these mutants (Magnuson et al. (1994) Semin. Cancer Biol., 5, 247-53). The Ras proto-oncogene requires a functionally intact C-Raf-1 proto-oncogene in order to transduce growth and differentiation signals initiated by receptor- and non-receptor-type tyrosine kinases in higher eukaryotes.

Activated Ras is necessary for the activation of the C-Raf-1 proto-oncogene, but the biochemical steps through which Ras activates the Raf-1 protein (Ser/Thr) kinase are now well characterised. It has been shown that inhibiting the effect of active Ras by inhibiting the Raf kinase signalling pathway by administration of deactivating antibodies to Raf kinase or by co-expression of dominant negative Raf kinase or dominant negative MEK (MAPKK), the substrate of Raf kinase, leads to reversion of transformed cells to the normal growth phenotype, see: Daum et al. (1994) Trends Biochem. Sci., 19, 474-80; Fridman et al. (1994) J. Biol. Chem., 269, 30105-8. Kolch et al. (1991) Nature, 349, 426-28 and for a review Weinstein-Oppenheimer et al. Pharm. & Therap. (2000), 88, 229-279.

Similarly, inhibition of Raf kinase (by antisense oligodeoxynucleotides) has been correlated in vitro and in vivo with inhibition of the growth of a variety of human tumour types (Monia et al., Nat. Med. 1996, 2, 668-75).

Raf serine- and threonine-specific protein kinases are cytosolic enzymes that stimulate cell growth in a variety of cellular systems (Rapp, U. R., et al. (1988) in The Oncogene Handbook; T. Curran, E. P. Reddy and A. Skalka (eds.) Elsevier Science Publishers; The Netherlands, pp. 213-253; Rapp, U. R., et al. (1988) Cold Spring Harbor Sym. Quant. Biol. 53:173-184; Rapp, U. R., et al. (1990) Inv Curr. Top. Microbiol. Immunol. Potter and Melchers (eds.), Berlin, Springer-Verlag 166:129-139).

Three isozymes have been characterised: C-Raf (Raf-1) (Bonner, T. I., et al. (1986) Nucleic Acids Res. 14:1009-1015). A-Raf (Beck, T. W., et al. (1987) Nucleic Acids Res. 15:595-609) and B-Raf (Qkawa, S., et al. (1998) Mol. Cell. Biol. 8:2651-2654; Sithanandam, G. et al. (1990) Oncogene: 1775). These enzymes differ in their expression in various tissues. Raf-1 is expressed in all organs and in all cell lines that have been examined, and A- and B-Raf are expressed in urogenital and brain tissues respectively (Storm, S. M. (1990) Oncogene 5:345-351).

Raf genes are proto-oncogenes can initiate malignant transformation of cells when expressed in specifically altered forms. Genetic changes that lead to oncogenic activation generate a constitutively active protein kinase by removal of or interference with an N-terminal negative regulatory domain of the protein (Heidecker, G., et al. (1990) Mol. Cell. Biol. 10:2503-2512; Rapp, U. R., et al. (1987) in Oncogenes and Cancer; S. A. Aaronson, J. Bishop, T. Sugimura, M. Terada, K. Toyoshima and P. K. Vogt (eds.) Japan Scientific Press, Tokyo). Microinjection into NIH 3T3 cells of oncogenically activated, but not wild-type, versions of the Raf protein prepared with *Escherichia coli* expression vectors results in morphological transformation and stimulates DNA synthesis (Rapp, U. R., et al. (1987) in Oncogenes and Cancer; S. A. Aaronson, J. Bishop, T. Sugimura, M. Terada, K. Toyoshima and P. K. Vogt (ed.) Japan Scientific Press, Tokyo; Smith, M. R., et al. (1990) Mol. Cell. Biol. 10:3828-3833).

Consequently, activated Raf-1 is an intracellular activator of cell growth. Raf-1 protein serine kinase is a candidate for the downstream effector of mitogen signal transduction, since Raf oncogenes overcome growth arrest resulting from a block of cellular Ras activity due either to a cellular mutation (Ras revertant cells) or microinjection of anti-Ras antibodies (Rapp, U. R., et al. (1988) in The Oncogene Handbook, T. Curran, E. P. Reddy and A. Skalka (eds.), Elsevier Science Publishers; The Netherlands, pp. 213-253; Smith, M. R., et al. (1986) Nature (London) 320:540-543).

C-Raf function plays a role in transformation by a variety of membrane-bound oncogenes and for growth stimulation by mitogens contained in serums (Smith, M. R., et al. (1986) Nature (London) 320:540-543). Raf-1 protein serine kinase activity is regulated by mitogens via phosphorylation (Morrison, D. K., et al. (1989) Cell 58:648-657), which also effects sub-cellular distribution (Olah, Z., et al. (1991) Exp. Brain Res. 84:403; Rapp, U. R., et al. (1988) Cold Spring Harbor Sym. Quant. Biol. 53:173-184. Raf-1 activating growth factors include platelet-derived growth factor (PDGF) (Morrison, D. K., et al. (1988) Proc. Natl. Acad. Sci. USA 85:8855-8859), colony-stimulating factor (Baccarini, M., et al. (1990) EMBO J. 9:3649-3657), insulin (Blackshear, P. J., et al. (1990) J. Biol. Chem. 265:12115-12118), epidermal growth factor (EGF) (Morrison, R. K., et al. (1988) Proc. Natl. Acad. Sci. USA 85:8855-8859), interleukin-2 (Turner, B. C., et al. (1991) Proc. Natl. Acad. Sci. USA 88:1227) and interleukin-3 and granulocyte macrophage colony-stimulating factor (Carroll, M. P., et al. (1990) J. Biol. Chem. 265:19812-19817).

After mitogen treatment of cells, the transiently activated Raf-1 protein serine kinase translocates to the perinuclear area and the nucleus (Olah, Z., et al. (1991) Exp. Brain Res. 84:403; Rapp, U. R., et al. (1988) Cold Spring Harbor Sym. Quant. Biol. 53:173-184). Cells containing activated Raf are altered in their pattern of gene expression (Heidecker, G., et al. (1989) in Genes and signal transduction in multistage carcinogenesis, N. Colburn (ed.), Marcel Dekker, Inc., New York, pp. 339-374) and Raf oncogenes activate transcription from Ap-I/PEA3-dependent promoters in transient transfection assays (Jamal, S., et al. (1990) Science 344:463466; Kaibuchi, K., et al. (1989) J. Biol. Chem. 264:20855-20858; Wasylyk, C., et al. (1989) Mol. Cell. Biol. 9:2247-2250).

There are at least two independent pathways for Raf-1 activation by extracellular mitogens: one involving protein kinase C (KC) and a second initiated by protein tyrosine kinases (Blackshear, P. J., et al. (1990) J. Biol. Chem. 265:12131-12134; Kovacina, K. S., et al. (1990) J. Biol. Chem. 265:12115-12118; Morrison, D. K., et al. (1988) Proc. Natl. Acad. Sci. USA 85:8855-8859; Siegel, J. N., et al. (1990) J. Biol. Chem. 265:18472-18480; Turner, B. C., et al. (1991) Proc. Natl. Acad. Sci. USA 88:1227). In each case, activation involves Raf-1 protein phosphorylation. Raf-1 phosphorylation may be a consequence of a kinase cascade amplified by autophosphorylation or may be caused entirely by autophosphorylation initiated by binding of a putative activating ligand to the Raf-1 regulatory domain, analogous to PKC activation by diacylglycerol (Nishizuka, Y. (1986) Science 233:305-312).

One of the principal mechanisms by which cellular regulation is effected is through the transduction of extracellular signals across the membrane that in turn modulate biochemical pathways within the cell. Protein phosphorylation represents one course by which intracellular signals are propagated from molecule to molecule resulting finally in a cellular response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is such a ubiquitous process within cells and since cellular phenotypes are largely influenced by the activity of these pathways, it is currently believed that a number of disease states and/or diseases are attributable to either aberrant activation or functional mutations in the molecular components of kinase cascades. Consequently, considerable attention has been devoted to the characterisation of these proteins and compounds that are able to modulate their activity (for a review see: Weinstein-Oppenheimer et al. Pharma. &. Therap., 2000, 88, 229-279).

The protein kinase PKB (also known as AKT and RAC-PK) is a member of the AKT/PKB family of serine/threonine kinases and has been shown to be involved in a diverse set of signalling pathways in human malignancy (Nicholson et al., Cell. Signal., 2002, 14, 381-395). PKB, like other members of the AKT/PKB family, is located in the cytosol of unstimulated cells and translocates to the cell membrane following stimulation. PKB translocation can be activated by a number of ligands, including platelet-derived growth factor, epidermal growth factor, basic fibroblast growth factor, cellular stress, such as, for example, heat shock and hyperosmolarity, as well as insulin (Bos, Trends Biochem. Sci., 1995, 20, 441-442), and other studies have shown that this activation is through PKB kinase which is wortmannin-sensitive (Franke et al., Science, 1997, 275, 665-668). Once located on the plasma membrane, PKB has been shown to mediate several functions within the cell, including apoptosis, the metabolic effects of insulin, induction of differentiation and/or proliferation, protein synthesis and stress responses (Alessi and Cohen, Curr. Opin. Genet. Dev., 1998, 8, 55-62; Downward, Curr. Opin. Cell Biol., 1998, 10, 262-267).

PKB was cloned independently in 1991 by three groups (Bellacosa et al., Science, 1991, 254, 274-277; Coffer and Woodgett, Eur. J. Biochem., 1991, 201, 475-481; Jones et al., Cell Regul., 1991, 2, 1001-1009), but its association with primary human gastric carcinoma was recognised as early as 1987 (Staal et al., Proc. Natl. Acad. Sci. USA, 1987, 84, 5034-5037). Sequencing of PKBα revealed homology within the kinase domains to the PKA (about 68%) and PKC isozymes (about 73%) (Jones et al., Proc. Natl. Acad. Sci. U.S.A., 1991, 88, 4171-5), a fact that led to its renaming as PKB. There are three cellular isoforms of PKB and two splice variants (PKBα, β, γ, $β_1$, $γ_1$; Brazil et al. Trends in Bio Sci, 2001, 26, 657-663). PKBα was found to be amplified or overexpressed in gastric adenocarcinomas and in a breast cancer cell line (Staal et al., Proc. Natl. Acad. Sci. U.S.A., 1987, 84, 5034-7; Jones et al., Cell Regul., 1991, 2, 1001-9). PKBβ is amplified or overexpressed in 3% of breast (Bellacosa et al., Int. J. Cancer, 1995 64, 280-5), 12% of pancreatic (Cheng et al., Proc. Natl. Acad. Sci. U.S.A., 1996, 93, 3636-41) and 15% of ovarian cancers (Bellacosa et al., Int. J. Cancer, 1995, 64, 280-5; Cheng et al., Proc. Natl. Acad. Sci. U.S.A., 1992, 89, 9267-71).

PKBγ is overexpressed in oestrogen receptor-deficient breast cancer and in androgen-independent prostate cell lines (Nakatani et al., J. Biol. Chem. 1999, 274, 21528-32).

It has been proposed that PKB is a gene which is involved in chromosomal rearrangement at chromosome band 14q32. This locus is known to under-go rearrangement in human T-cell malignancies, such as, for example, prolymphocytic leukaemias and mixed lineage childhood leukaemias (Staal et al., Genomics, 1988, 2, 96-98).

PKB also plays a role in the prevention of "programmed cell death" or apoptosis by inhibitory phosphorylation of ASK-1, Bad, Caspase9 and FKHR (for review see Nicholson et al., Cell Signalling 2001, 14, 281-395). It has been shown that PKB provides cells with a survival signal (for review see Lawlor et al., J. of Cell Science 2001, 114, 2903-2910) in order to protect them from a number of agents, including UV radiation (Dudek et al., Science, 1997, 275, 661-665), withdrawal of IGF1 from neuronal cells, detachment from the extracellular matrix, stress and heat shock (Alessi and Cohen, Curr. Opin. Genet. Dev., 1998, 8, 55-62).

The dual-specific phosphatase PTEN (phosphatase and tensin homologue deleted on chromosome ten) increases the PtdIns(3, 4, 5)P$_3$ level in the cell by dephosphorylation of PtdIns(3, 4, 5)P$_3$. PtdIns(3, 4, 5)P$_3$ binds to the PH domain (Pleckstrin homology domain) of PKB. This binding is an essential step for membrane translocation and activation of PKB. PTEN is a tumour suppressor gene mutated in a large proportion of glioblastoma and melanoma cell lines, advanced prostate carcinomas and endometrial carcinomas. Furthermore, it is deleted in >80% of patients with hereditary conditions, such as, for example, Cowden's disease, Lhermitte-Duclos syndrome and Bannayan-Zonana syndrome. The patients display a number of similar features, including multiple benign tumours (harmatomas) and increased susceptibility to breast and thyroid malignancies (Di Cristofano et al. Cell, 2000, 100, 387-390).

Cell lines derived from PTEN$^{+/-}$ heterozygous mice (PTEN$^{-/-}$ heterozygous mice are not viable) show increased PtdIns(3, 4, 5)P$_3$ levels paralleled by increased PKB activity, with concomitant decreased sensitivity to apoptosis (Di Christofano et al. Nat. Genet. 1998, 19, 348-355; Stambolic et al., Cell, 1998, 95, 29-39, Myers et al., Proc. Natl. Acad. Si. U.S.A., 1998, 96 13513-13518).

PKB is also able to promote cell cycle progression by inhibiting p21 cell cycle inhibitor (Zhou et al.; Nat. Cell Biol., 2002, 3, 245-252).

These findings may explain the overexpression of PKB observed in cancer cells which allows preferential survival and proliferation of the carcinomas by preventing the normal progression to apoptosis.

At present, there are no known therapeutic agents which effectively inhibit the activity of PKB. Consequently, there remains a long felt need for agents which are capable of effectively inhibiting PKB function for the activation of pro-apoptotic proteins in all kinds of cancer as chemotherapeutic agents.

The identification of small compounds which specifically inhibit, regulate and/or modulate signal transduction of tyrosine kinases and/or Raf kinases is therefore desirable and an aim of the present invention.

It has been found that the compounds of the formula I and salts and solvates thereof have very valuable pharmacological properties while being well tolerated. In particular, they exhibit tyrosine kinase inhibiting properties.

It has furthermore been found that the compounds of the formula I, and salts and solvates thereof, which are generally described as chromenone derivatives, are inhibitors of the enzyme Raf kinase. Since the enzyme is a downstream effector of p21$^{ras}$, the inhibitors prove to be suitable in pharmaceutical compositions for use in human or veterinary medicine where inhibition of the Raf kinase pathway is indicated, for example in the treatment of tumours and/or cancerous cell growth mediated by Raf kinase. In particular, the compounds are suitable for the treatment of human and animal solid cancers, for example murine cancer, since the progression of these cancers is dependent upon the Ras protein signal transduction cascade and therefore susceptible to treatment by interruption of the cascade, i.e. by inhibiting Raf kinase. Accordingly, the compound of the formula I or a pharmaceutically acceptable salt or solvate thereof is administered for the treatment of diseases mediated by the Raf kinase pathway, especially cancer, including solid cancers, such as, for example, carcinomas (for example of the lungs, pancreas, thyroid, bladder or colon), myeloid diseases (for example myeloid leukaemia) or adenomas (for example villous colon adenoma), pathological angiogenesis and metastatic cell migration. The compounds are furthermore suitable for the treatment of complement activation dependent chronic inflammation (Niculescu et al. (2002) Immunol. Res., 24:191-199) and HIV-1 (human immunodeficiency virus type 1) induced immunodeficiency (Popik et al. (1998) J Virol, 72: 6406-6413).

Surprisingly, it has been found that compounds according to the invention are able to interact with signalling pathways, especially the signalling pathways described herein and preferably the Raf kinase signalling pathway. Chromenone derivatives according to the invention preferably exhibit an advantageous biological activity which is easily demonstrated in enzyme-based assays, for example assays as described herein. In such enzyme-based assays, chromenone derivatives according to the invention exhibit an effect, preferably an inhibiting effect, which is usually documented by IC$_{50}$ values in a suitable range, preferably in the micromolar range and more preferably in the nanomolar range.

As discussed herein, these signalling pathways are relevant for various diseases. Accordingly, chromenone derivatives are suitable for the prophylaxis and/or treatment of diseases that are dependent on the said signailing pathways by interacting with one or more of the said signalling pathways.

The present invention therefore in one aspect relates to compounds according to the invention as promoters or inhibitors, preferably as inhibitors, of the signalling pathways described herein. The invention therefore preferably relates to compounds according to the invention as promoters or inhibitors, preferably as inhibitors, of the Raf kinase pathway. The invention therefore more preferably relates to derivatives according to the invention as promoters or inhibitors, preferably as inhibitors, of Raf kinase. The invention still more preferably relates to compounds according to the invention as promoters or inhibitors, preferably as inhibitors, of one or more Raf kinases selected from the group consisting of A-Raf, B-Raf and C-Raf-1. The invention particularly preferably relates to compounds according to the invention as promoters or inhibitors, preferably as inhibitors, of C-Raf-1.

The present invention furthermore relates to the use of one or more compounds according to the invention in the treatment and/or prophylaxis of diseases, preferably the diseases described herein, that are caused, mediated and/or propagated by Raf kinases and in particular diseases that are caused, mediated and/or propagated by Raf kinases selected from the group consisting of A-Raf, B-Raf and C-Raf-1. The diseases discussed herein are usually divided into two groups, hyperproliferative and nonhyperproliferative diseases. In this connection, psoriasis, arthritis, inflammation, endometriosis, scarring, benign prostatic hyperplasia, immunological diseases, autoimmune diseases and immunodeficiency diseases are to be regarded as non-cancerous diseases, of which arthritis, inflammation, immunological diseases, autoimmune diseases and immunodeficiency diseases are usually regarded as non-hyperproliferative diseases. In this connection, brain cancer, lung cancer, squamous cell cancer, bladder cancer, gastric cancer, pancreatic cancer, hepatic cancer, renal cancer, colorectal cancer, breast cancer, head cancer, neck cancer, oesophageal cancer, gynaecological cancer, thyroid cancer, lymphoma, chronic leukaemia and acute leukaemia are to be regarded as cancerous diseases, all of which are usually regarded as hyperproliferative diseases. Especially cancerous cell growth and especially cancerous cell growth mediated by Raf kinase is a disease which is a target of the present invention. The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases as well as to a method for the treatment of the said diseases which comprises the administration of one or more compounds according to the invention to a patient in need of such an administration.

In a comparative measurement, it has furthermore been found that the compounds of the formula I act as PKB inhibitors. This action can be demonstrated, for example, by a method described by Alessi et al. EMBO L. 1996, 15, 6541-6551.

It can be shown that the compounds according to the invention have an antiproliferative action in vivo. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both prevention of diseases and treatment of pre-existing conditions. The prevention of proliferation is achieved by administration of the compounds according to the invention prior to the development of overt disease, for example to prevent the growth of tumours, prevent metastatic growth, diminish restenosis associated with cardiovascular surgery, etc. Alternatively, the compounds are used for the treatment of on-going diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For the identification of kinase inhibitors, various assay systems are available. In scintillation proximity assay (Sorg et al., J. of Biomolecular Screening, 2002, 7, 11-19) and flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J., just about to be published, manuscript BJ20020786).

There are many diseases associated with deregulation of cellular proliferation and cell death (apoptosis). The conditions of interest include, but are not limited to, the following. The compounds according to the invention are suitable for the treatment of a number of conditions where there is proliferation and/or migration of smooth muscle cells and/or inflammatory cells into the intimal layer of a vessel, resulting in restricted blood flow through that vessel, for example in the case of neointimal occlusive lesions. Occlusive vascular diseases of interest include atherosclerosis, graft coronary vascular disease after transplantation,-vein graft stenosis, peri-anastomatic prosthetic restenosis, restenosis after angioplasty or stent placement, and the like.

The compounds according to the invention are, in addition, suitable as food supplements, for the treatment of diseases and/or dysfunctions which are characterised by oxidative stress conditions and as sunscreens in cosmetic formulations.

PRIOR ART

WO 92/20642 describes bis-mono- and -bicyclic aryl and heteroaryl compounds which are able to inhibit tyrosine kinase. Chromenone derivatives are not disclosed.

Chromenone derivatives as constituents of photographic materials are disclosed in Patent No. JP 07191431 (Application No. JP 0347126).

Fluorine-containing heteroaryl flavonoids having a fungicidal action are disclosed in Indian Journal of Chemistry, Section B: Organic Chemistry Including Medicinal Chemistry (1987), 26B(5), 493-5.

Chromenone derivatives which are described in the literature, but not in connection with tyrosine kinase inhibition are listed below:
CAS RN 477545-79-2 1-[(4-oxo-4H-1-benzopyran-2-yl)carbonyl]-4-phenylpiperazine;
CAS RN 476298-55-2 1-[(4-oxo-4H-1-benzopyran-2-yl)carbonyl]-3,5-dimethylpiperidine;
CAS RN 380469-63-6 10-[(4-oxo-4H-1-benzopyran-2-yl)carbonyl]phenothiazine;
CAS RN 380328-67-6 ethyl 1-[(4-oxo-4H-1-benzopyran-2-yl)carbonyl]4-piperidinecarboxylate;
CAS RN 361166-59-8 1-[(4-oxo-4H-1-benzopyran-2-yl)carbonyl]-1H-indole;
CAS RN 361166-57-6 1,2,3,4-tetrahydro-2-[(4-oxo-4H-1-benzopyran-2-yl)carbonyl]isoquinoline;
CAS RN 361166-50-9 1,2,3,4-tetrahydro-2-[(4-oxo-4H-1-benzopyran-2-yl)carbonyl]quinoline;
CAS RN 361166-57-6 4-[(6-bromo-4-oxo-4H-1-benzopyran-2-yl)carbonyl]morpholine;
CAS RN 35266741-5 4-[(6-chloro-4-oxo-4H-1-benzopyran-2-yl)carbonyl]morpholine;

CAS RN 352667-39-1 1-[(6-bromo-4-oxo-4H-1-benzopyran-2-yl)carbonyl]pyrrolidine;
CAS RN 352667-38-0 1-[(6-bromo-4-oxo-4H-1-benzopyran-2-yl)carbonyl]piperidine; and
CAS RN 113734-98-8 2-[(8-bromo-6-fluoro-4-oxo-4H-1-benzopyran-2-yl)carbonyl]thiophene.

SUMMARY OF THE INVENTION

In one aspect, the invention relates to compounds of the formula I

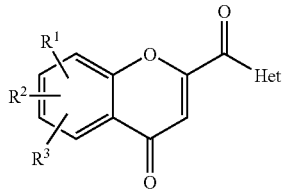

in which
R$^1$ is H, —OH, —OA, phenoxy, Ar, —O—CO-A, SO$_3$H, SO$_3$A, —OSO$_3$H, —OSO$_3$A, —OSO$_2$A, SO$_2$A, COOH, COOA, CONH$_2$, NHSO$_2$A, COA, CHO or SO$_2$NH$_2$,
R$^2$ is H, —OH, —OA, phenoxy, Ar, —O—CO-A, SO$_3$H, SO$_3$A, —OSO$_3$H, —OSO$_3$A, —OSO$_2$A, SO$_2$A, Hal, COOH, COOA, CONH$_2$, NHSO$_2$A, COA, CHO or SO$_2$NH$_2$,
R$^3$ is H, —OH, —OA, phenoxy, Ar, —O—CO-A, SO$_3$H, SO$_3$A, —OSO$_3$H, —OSO$_3$A, —OSO$_2$A, SO$_2$A, Hal, COOH, COOA, CONH$_2$, NHSO$_2$A, COA, CHO or SO$_2$NH$_2$,
R$^1$ and R$^2$ together are alternatively methylenedioxy or ethylenedioxy,
Het is a monocyclic or bicyclic, saturated, unsaturated or aromatic heterocyclic ring having from 1 to 4 N, O and/or S atoms, which may be unsubstituted or mono-, di- or trisubstituted by carbonyl oxygen, =S, =NH, Hal, A, —(CH$_2$)$_o$—Ar, —(CH$_2$)$_o$—cycloalkyl, —(CH$_2$)$_o$—OH, —(CH$_2$)$_o$—NH$_2$, NO$_2$, CN, —(CH$_2$)$_o$—COOH, —(CH$_2$)$_o$—COOA, —(CH$_2$)$_o$—CONH$_2$, —(CH$_2$)$_o$—N HCOA, NHCONH$_2$, —(CH$_2$)$_o$—NHSO$_2$A, CHO, COA', SO$_2$NH$_2$ and/or S(O)$_o$A,
Ar is phenyl, naphthyl or biphenyl, each of which is unsubstituted or mono-, di- or trisubstituted by Hal, A, OH, OA, NH$_2$, NO$_2$, CN, COOH, COOA, CONH$_2$, NHCOA, NHCONH$_2$, NHSO$_2$A, CHO, COA, SO$_2$NH$_2$ or S(O)$_o$A,
A is unbranched or branched alkyl having 1-10 carbon atoms, where 1-7H atoms may be replaced by F,
A' is alkyl having from 1 to 6 carbon atoms or benzyl,
Hal is F, Cl, Br or I, and
o is 0, 1 or 2, and pharmaceutically usable derivatives, solvates, salts and stereoisomers thereof, including mixtures thereof in all ratios.

The invention relates to the compounds of the formula I and salts thereof and to a process for the preparation of compounds of the formula I and to pharmaceutically usable derivatives, solvates, salts and stereoisomers thereof, characterised in that a) firstly a compound of the formula II

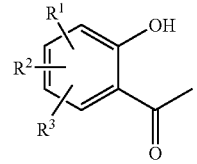

in which
R$^1$ is —OH or —OA,
R$^2$ is H, —OH, —OA, phenoxy, —O—CO-A, —OSO$_3$H, —OSO$_3$A, —OSO$_2$A or Hal,
R$^3$ is H, is reacted with a compound of the formula III

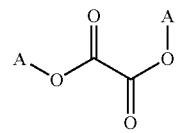

in which A is alkyl having 1, 2, 3, 4, 5 or 6 carbon atoms, to give a compound of the formula IV

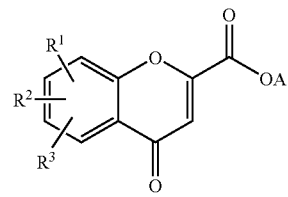

in which A, R$^1$, R$^2$ and R$^3$ are as defined above,
b) subsequently the ester IV is reacted with a compound of the formula V M-Het          V in which Het is chromen-2-onyl, benzothiazolyl, thienyl, pyridinyl, pyrimidinyl, pyrazinyl, indolyl, furyl, pyrrolyl, isoxazolyl, imidazolyl, thiazolyl, triazolyl, tetrazolyl, quinolyl or isoquinolyl, each of which is unsubstituted or mono- or disubstituted by Hal and/or A, and M is sodium, potassium or lithium, to give a compound of the formula 1, and/or c) a base or acid of the formula I is converted into one of its salts, or solvates.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, monohydrates or dihydrates or alkoxides.

The invention also relates to pharmaceutically usable derivatives which is taken to mean, for example, the salts of the compounds according to the invention and also so-called prodrug compounds. The term prodrug derivatives is taken to mean compounds of the formula I which have been modified by means of, for example, alkyl or acyl groups, sugars or oligopeptides and which are rapidly cleaved in the organism to form the effective compounds according to the invention. These also include biodegradable polymer derivatives of the compounds according to the invention, as described, for example, in Int. J. Pharm. 115, 61-67 (1995).

The invention also relates to mixtures of the compounds of the formula I according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

For all radicals which occur more than once, such as, for example, A, their meanings are independent of one another.

A is alkyl, is unbranched (linear) or branched and has 1, 2, 3, 4, 5, 6, 7, 8, 9 or 10 carbon atoms. A is preferably methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl. A is very particularly preferably alkyl having 1, 2, 3, 4, 5 or 6 carbon atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

A' is preferably alkyl having 1, 2, 3, 4, 5 or 6 carbon atoms, preferably methyl, ethyl, propyl, isopropyl, butyl, isobutyl, sec-butyl, tert-butyl, pentyl, hexyl or benzyl.

OA is alkoxy and is preferably, for example, methoxy, ethoxy, propoxy, isopropoxy, butoxy, trifluoromethoxy or cyclopentoxy.

—COA (acyl) is preferably acetyl, propionyl, furthermore also butyryl, pentanoyl, hexanoyl or, for example, benzoyl.

Hal is preferably F, Cl or Br, but also I.

Ar is, for example, unsubstituted phenyl, naphthyl or biphenyl, furthermore preferably phenyl, naphthyl or biphenyl, each of which is mono-, di- or trisubstituted by, for example, A, fluorine, chlorine, bromine, iodine, hydroxyl, methoxy, ethoxy, propoxy, butoxy, pentyloxy, hexyloxy, nitro, cyano, formyl, acetyl, propionyl, trifluoromethyl, amino, methylamino, ethylamino, dimethylamino, diethylamino, benzyloxy, sulfonamido, methylsulfonamido, ethylsulfonamido, propylsulfonamido, butylsulfonamido, dimethylsulfonamido, phenylsulfonamido, carboxyl, methoxycarbonyl, ethoxycarbonyl or aminocarbonyl. Ar is very particularly preferably phenyl.

Het, apart from the possible substituents, is, for example, 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, 4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl, 2,1,3-benzoxadiazol-5-yl or chromenyl. The heterocyclic radicals may also be partially or fully hydrogenated. Het can thus also be, for example, 2,3-dihydro-2-, -3-, 4- or -5-furyl, 2,5-dihydro-2-, -3-, 4- or -5-furyl, tetrahydro-2- or -3-furyl, 1,3-dioxolan-4-yl, tetrahydro-2- or -3-thienyl, 2,3-dihydro-1-, -2-, -3-, 4- or -5-pyrrolyl, 2,5-dihydro-1-, -2-, -3-, 4- or -5-pyrrolyl, 1-, 2- or 3-pyrrolidinyl, tetrahydro-1-, -2- or 4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, 4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, 4- or -5-yl, hexahydro-1-, -3- or 4-pyridazinyl, hexahydro-1-, -2-, -4- or -5-pyrimidinyl, 1-, 2- or 3-piperazinyl, 1,2,3,4-tetrahydro-1-, -2-, -3-, 4-, -5-, -6-, -7- or -8-quinolyl, 1,2,3,4-tetrahydro-1-, -2-, -3-, 4-, -5-, -6-, -7 - or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylened ioxyphenyl, 2,3-ethylenedioxyphenyl, 3,4-ethylenedioxyphenyl, 3,4-(difluoromethylenedioxy) phenyl, 2,3-dihydrobenzofuran-5- or -6-yl, 2,3-(2-oxo-methylenedioxy)phenyl or 3,4-dihydro-2H-1,5-benzodioxepin-6- or -7-yl, furthermore preferably 2,3-dihydrobenzofuranyl or 2,3-dihydro-2-oxo-furanyl.

Het is particularly preferably chromen-2-onyl, benzothiazolyl, thienyl, pyridinyl, pyrimidinyl, pyrazinyl, indolyl, furyl, pyrrolyl, isoxazolyl, imidazolyl, thiazolyl, triazolyl, tetrazolyl, quinolyl or isoquinolyl, each of which is unsubstituted or mono- or disubstituted by Hal and/or A.

$R^1$ is preferably —OH, —OA, phenoxy, —O—CO-A, —OSO$_3$H, —OSO$_3$A or —OSO$_2$A, very particularly preferably —OH or —OA.

$R^2$ is preferably H, —OH, —OA, phenoxy, —O—CO-A, —OSO$_3$H, —OSO$_3$A, —OSO$_2$A or Hal.

$R^3$ is preferably H.

$R^1$ and $R^2$ together are preferably alternatively methylenedioxy.

The compounds of the formula I can occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds can be expressed by the following sub-formulae Ia to Ig, which conform to the formula I and in which the radicals not designated in greater detail are as defined for the formula 1, but in which in Ia $R^1$ is —OH, —OA, phenoxy, —O—CO-A, —OSO$_3$H, —OSO$_3$A or —OSO$_2$A, in Ib $R^1$ is —OH or —OA, in Ic $R^1$ is —OH, —OA, phenoxy, —O—CO-A, —OSO$_3$H, —OSO$_3$A or —OSO$_2$A, $R^2$ is H, —OH, —OA, phenoxy, —O—CO-A, —OSO$_3$H, —OSO$_3$A, —OSO$_2$A or Hal, $R^3$ is H, $R^1$ and $R^2$ together are alternatively methylenedioxy or ethylenedioxy, in Id $R^1$ is —OH, —OA, phenoxy, —O—CO-A, —OSO$_3$H, —OSO$_3$A or —OSO$_2$A, $R^2$ is H, —OH, —OA, phenoxy, —O—CO-A, —OSO$_3$H, —OSO$_3$A, —OSO$_2$A or Hal, $R^3$ is H, $R^1$ and $R^2$ together are alternatively methylenedioxy or ethylenedioxy, Het is a monocyclic or bicyclic, saturated, unsaturated or aromatic heterocyclic ring having from 1 to 4 N, O and/or S atoms, which may be unsubstituted or mono-, di- or trisubstituted by Hal and/or A, in Ie $R^1$ is —OH, —OA, phenoxy, —O—CO-A, —OSO$_3$H, —OSO$_3$A or —OSO$_2$A, $R^2$ is H, —OH, —OA, phenoxy, —O—CO-A, —OSO$_3$H, —OSO$_3$A, —OSO$_2$A or Hal, $R^3$ is H, $R^1$ and $R^2$ together are alternatively methylenedioxy or ethylenedioxy, Het is a monocyclic or bicyclic, aromatic heterocyclic ring having from 1 to 3 N, O and/or S atoms, which may be unsubstituted or mono-, di- or trisubstituted by Hal and/or A, in If $R^1$ is —OH or —OA, $R^2$ is H, —OH, —OA, phenoxy, —O—CO-A, —OSO$_3$H, —OSO$_3$A, —OSO$_2$A or Hal, $R^3$ is H, $R^1$ and $R^2$ together are alternatively methylenedioxy or ethylenedioxy, Het is chromen-2-onyl, benzothiazolyl, thienyl, pyridinyl, pyrimidinyl, pyrazinyl, indolyl, furyl, pyrrolyl, isoxazolyl, imidazolyl, thiazolyl, triazolyl, tetrazolyl, quinolyl or isoquinolyl, each of which is unsubstituted or mono- or disubstituted by Hal and/or A, A is unbranched or branched alkyl having 1-6 carbon atoms, where 1-5H atoms may be replaced by F, in Ig $R^1$ is —OH or —OA, $R^2$ is H, —OH, —OA or Hal, $R^3$ is H, $R^1$ and $R^2$ together are alternatively methylenedioxy or ethylenedioxy, Het is benzothiazolyl, pyridinyl, pyrimidinyl, pyrazinyl, indolyl, furyl, pyrrolyl, isoxazolyl, imidazolyl or thiazolyl, each of which is unsubstituted or mono- or disubstituted by Hal and/or A, A is unbranched or branched alkyl having 1-6 carbon atoms, where 1-5H atoms may be replaced by F, and pharmaceutically usable derivatives, solvates, salts and stereoisomers thereof, including mixtures thereof in all ratios.

The invention relates in particular to the following compounds of the formula I:

6-hydroxy-2-(1-methyl-1H-imidazole-2-carbonyl)chromen-4-one, 5,7-dihydroxy-2-(1-methyl-1H-imidazole-2-carbonyl)chromen-4-one, 7-hydroxy-2-(1-methyl-1H-imidazole-2-carbonyl)chromen-4-one, 6-(1-methyl-1H-imidazole-2-carbonyl)-1,3-dioxolo[4,5 g]chromen-8-one, 5,7-dihydroxy-2-(pyridine-2-carbonyl)chromen-4-one, 6-hydroxy-2-(pyridine-2-carbonyl)chromen-4-one, 6-hydroxy-2-(3,5-dichloropyrazine-2-carbonyl)chromen-4-one, and 6-hydroxy-2-(benzothiazolyl-2-carbonyl)chromen-4-one, and pharmaceutically usable derivatives, solvates, salts and stereoisomers thereof are, including mixtures thereof in all ratios.

The compounds of the formula I and also the starting materials for the preparation thereof, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants which are known per se, but are not mentioned here in greater detail.

If desired, the starting materials can also be formed in situ so that they are not isolated from the reaction mixture, but instead are immediately converted further into the compounds of the formula I.

The starting compounds of the formulae II and III are generally known. If they are novel, they can, however, be prepared by methods known per se.

Compounds of the formula I can preferably be obtained by firstly reacting compounds of the formula II with compounds of the formula III to give compounds of the formula IV.

The reaction is carried out by methods which are known to the person skilled in the art. The reaction is initially carried out in a suitable alcohol in the presence of an alkali or alkaline-earth metal alkoxide, for example in ethanol/sodium ethoxide or methanol/potassium methoxide.

In principle, the following inert solvents can also be used.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Depending on the conditions used, the reaction time is between a few minutes and 14 days, and the reaction temperature is between about –30° and 140°., normally between –10° and 90°, in particular between about 0° and about 70°.

The cyclisation to give the compound of the formula IV is carried out with acid catalysis, by addition of suitable mineral acids, such as, for example, hydrochloric acid, phosphoric acid or sulfuric acid.

The reaction time and temperature are preferably as indicated above.

The esters of the formula IV are reacted with the compounds of the formula V by standard methods in an inert solvent to give the compounds of the formula I.

The compound of the formula V employed is preferably Li-Het.

The inert solvent, reaction time and temperature are preferably as indicated above, with reaction in THF at from –80 to –75° C. being particularly preferred.

A base of the formula I can be converted into the associated acid-addition salt using an acid, for example by reaction of equivalent amounts of the base and the acid in an inert solvent, such as ethanol, followed by evaporation. Suitable acids for this reaction are, in particular, those which give physiologically acceptable salts. Thus, it is possible to use inorganic acids, for example sulfuric acid, nitric acid, hydrohalic acids, such as hydrochloric acid or hydrobromic acid, phosphoric acids, such as orthophosphoric acid, or sulfamic acid, furthermore organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids and laurylsulfuric acid. Salts with physiologically unacceptable acids, for example picrates, can be used for the isolation and/or purification of the compounds of the formula I.

On the other hand, compounds of the formula I can be converted into the corresponding metal salts, in particular alkali metal or alkaline-earth metal salts, or into the corresponding ammonium salts using bases (for example sodium hydroxide, potassium hydroxide, sodium carbonate or potassium carbonate). It is also possible to use physiologically acceptable organic bases, such as, for example, ethanolamine.

Compounds of the formula I according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds of the formula I and/or physiologically acceptable salts thereof for the preparation of a medicament (pharmaceutical preparation), in particular by non-chemical methods. They can be converted here into a suitable dosage form together with at least one solid, liquid and/or semi-liquid excipient or adjuvant and, if desired, in combination with one or more further active ingredients.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

These preparations can be used as medicaments in human or veterinary medicine. Suitable excipients are organic or inorganic substances which are suitable for enteral (for example oral), parenteral or topical administration and do not react with the novel compounds, for example water, vegetable oils, benzyl alcohols, alkylene glycols, polyethylene glycols, glycerol triacetate, gelatine, carbohydrates, such as lactose or starch, magnesium stearate, talc or Vaseline. Suitable for oral administration are, in particular, tablets, pills, coated tablets, capsules, powders, granules, syrups, juices or drops, suitable for rectal administration are suppositories, suitable for parenteral administration are solutions, preferably oil-based or aqueous solutions, furthermore suspensions, emulsions or implants, and suitable for topical application are ointments, creams or powders or also as nasal sprays. The novel compounds may also be lyophilised and the resultant lyophilisates used, for example, to prepare injection preparations. The preparations indicated may be sterilised and/or comprise adjuvants, such as lubricants, preservatives, stabilisers and/or wetting agents, emulsifiers, salts for modifying the osmotic pressure, buffer substances, colorants and flavours and/or a plurality of further active ingredients, for example one or more vitamins.

The invention furthermore relates to medicaments comprising at least one compound of the formula I and/or pharmaceutically usable derivatives, solvates, salts and stereoisomers thereof, including mixtures thereof in all ratios, and at least one further medicament active ingredient.

The invention also relates to a set (kit) consisting of separate packs of
(a) an effective amount of a compound of the formula I and/or pharmaceutically usable derivatives, solvates, salts and stereoisomers thereof, including mixtures thereof in all ratios, and
(b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

The invention also relates to the use of compounds of the following formula I according to claim 1

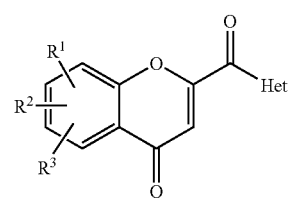

in which
$R^1$ is H, —OH, —OA, phenoxy, Ar, —O—CO-A, $SO_3H$, $SO_3A$, —$OSO_3H$, —$OSO_3A$, —$OSO_2A$, $SO_2A$, Hal, COOH, COOA, $CONH_2$, $NHSO_2A$, COA, CHO or $SO_2NH_2$, $R^2$ is H, —OH, —OA, phenoxy, Ar, —O—CO-A, $SO_3H$, $SO_3A$, —$OSO_3H$, —$OSO_3A$, —$OSO_2A$, $SO_2A$, Hal, COOH, COOA, $CONH_2$, $NHSO_2A$, COA, CHO or $SO_2NH_2$, $R^3$ is H, —OH, —OA, phenoxy, Ar, —O—CO-A, $SO_3H$, $SO_3A$, —$OSO_3H$, —$OSO_3A$, —$OSO_2A$, $SO_2A$, Hal, COOH, COOA, $CONH_2$, $NHSO_2A$, COA, CHO or $SO_2NH_2$, $R^1$ and $R^2$ together are alternatively methylenedioxy or ethylenedioxy, Het is a monocyclic or bicyclic, saturated, unsaturated or aromatic heterocyclic ring having from 1 to 4 N, O and/or S atoms, which may be unsubstituted or mono-, di- or trisubstituted by carbonyl oxygen, =S, =NH, Hal, A, —(CH$_2$)$_o$—Ar, —(CH$_2$)$_o$—cycloalkyl, —(CH$_2$)$_o$—OH, —(CH$_2$)$_o$—NH$_2$, NO$_2$, CN, —(CH$_2$)$_o$—COOH, —(CH$_2$)$_o$—COOA, —(CH$_2$)$_o$—CON H$_2$, —(CH$_2$)$_o$—N HCOA, N HCON H$_2$, —(CH$_2$)$_o$—NHSO$_2$A, CHO, COA', SO$_2$NH$_2$ and/or S(O)$_o$A, Ar is phenyl, naphthyl or biphenyl, each of which is unsubstituted or mono-, di- or trisubstituted by Hal, A, OH, OA, NH$_2$, NO$_2$, CN, COOH, COOA, CONH$_2$, NHCOA, NHCONH$_2$, NHSO$_2$A, CHO, COA, SO$_2$NH$_2$ or S(O)$_o$A, A is unbranched or branched alkyl having 1-10 carbon atoms, where 1-7H atoms may be replaced by F, A' is alkyl having from 1 to 6 carbon atoms or benzyl, Hal is F, Cl, Br or I, o is 0, 1 or 2, and pharmaceutically usable derivatives, solvates, salts and stereoisomers thereof, including mixtures thereof in all ratios, for the preparation of a medicament for the treatment of diseases in which the inhibition, regulation and/or modulation of kinase signal transduction plays a role.

Tyrosine kinases and/or Raf kinases are preferred here.

The invention furthermore relates to the use of compounds of the formula I as described above, and pharmaceutically usable derivatives, solvates, salts and stereoisomers thereof, including mixtures thereof in all ratios, for the preparation of a medicament for the treatment of diseases which are influenced by inhibition of tyrosine kinase by the compounds of the formula I.

The invention furthermore relates to the use of compounds of the formula I as described above, and pharmaceutically usable derivatives, solvates, salts and stereoisomers thereof, including mixtures thereof in all ratios, for the preparation of a medicament for the treatment of diseases which are caused, mediated and/or propagated by Raf kinases, where the Raf kinase is selected from the group consisting of A-Raf, B-Raf and Raf-1.

The meanings and preferred embodiments generally with respect to uses correspond to those mentioned elsewhere in the specification with respect to the compounds.

Accordingly, the invention relates in particular to the uses of the compounds of the formula I as described above in which at least one of the radicals mentioned has one of the preferred meanings indicated above. Some preferred uses of groups of compounds can be expressed by the following sub-formulae Ia to Ig, which conform to the formula I and in which the radicals not designated in greater detail are as defined for the formula I as described above, but in which in Ia R$^1$ is H, —OH, —OA, phenoxy, —O—CO-A, —OSO$_3$H, —OSO$_3$A, —OSO$_2$A or Hal;

in Ib R$^1$ is H, —OH, —OA, phenoxy, —O—CO-A, —OSO$_3$H, —OSO$_3$A, —OSO$_2$A or Hal,
R$^2$ is H, —OH, —OA, phenoxy, —O—CO-A, —OSO$_3$H, —OSO$_3$A, —OSO$_2$A or Hal,
R$^3$ is H,
R$^1$ and R$^2$ together are alternatively methylenedioxy or ethylenedioxy;

in Ic R$^1$ is —OH, —OA, phenoxy, —O—CO-A, —OSO$_3$H, —OSO$_3$A, —OSO$_2$A or Hal,
R$^2$ is H, —OH, —OA, phenoxy, —O—CO-A, —OSO$_3$H, —OSO$_3$A, —OSO$_2$A or Hal,
R$^3$ is H, R$^1$ and R together are alternatively methylenedioxy or ethylenedioxy,
Het is a monocyclic or bicyclic, saturated, unsaturated or aromatic heterocyclic ring having from 1 to 4 N, O and/or S atoms, which may be unsubstituted or mono-, di- or trisubstituted by Hal and/or A;

in Id R$^1$ is —OH, —OA, phenoxy, —O—CO-A, —OSO$_3$H, —OSO$_3$A or —OSO$_2$A,
R$^2$ is H, —OH, —OA, phenoxy, —O—CO-A, —OSO$_3$H, —OSO$_3$A, —OSO$_2$A or Hal,
R$^3$ is H,
R$^1$ and R$^2$ together are alternatively methylenedioxy or ethylenedioxy,
Het is a monocyclic or bicyclic, saturated, unsaturated or aromatic heterocyclic ring having from 1 to 4 N, O and/or S atoms, which may be unsubstituted or mono-, di- or trisubstituted by Hal and/or A;

in Ie R$^1$ is —OH, —OA, phenoxy, —O—CO-A, —OSO$_3$H, —OSO$_3$A, —OSO$_2$A or Hal,
R$^2$ is H, —OH, —OA, phenoxy or —O—CO-A,
R$^3$ is H,
R$^1$ and R together are alternatively methylenedioxy or ethylenedioxy,
Het is a monocyclic or bicyclic, aromatic heterocyclic ring having from 1 to 3 N, O and/or S atoms, which may be unsubstituted or mono-, di- or trisubstituted by Hal and/or A;

in If R$^1$ is —OH or —OA,
R$^2$ is H, —OH, —OA, phenoxy, —O—CO-A, —OSO$_3$H, —OSO$_3$A, —OSO$_2$A or Hal,
R$^3$ is H,
R$^1$ and R$^2$ together are alternatively methylenedioxy or ethylenedioxy,
Het is a monocyclic or bicyclic, aromatic heterocyclic ring having from 1 to 4 N, O and/or S atoms, which may be unsubstituted or mono-, di- or trisubstituted by Hal and/or A;

in Ig R$^1$ is —OH or —OA,
R$^2$ is H, —OH, —OA, phenoxy, —O—CO-A, —OSO$_3$H, —OSO$_3$A, —OSO$_2$A or Hal,
R$^3$ is H,
R$^1$ and R$^2$ together are alternatively methylenedioxy or ethylenedioxy,
Het is chromen-2-onyl, benzothiazolyl, thienyl, pyridinyl, pyrimidinyl, pyrazinyl, indolyl, furyl, pyrrolyl, isoxazolyl, imidazolyl, thiazolyl, triazolyl, tetrazolyl, quinolyl or isoquinolyl, each of which is unsubstituted or mono- or disubstituted by Hal and/or A,
A is unbranched or branched alkyl having 1-6 carbon atoms, where 1-5H atoms may be replaced by F;

and pharmaceutically usable derivatives, solvates, salts and stereoisomers thereof, including mixtures thereof in all ratios.

The present compounds are suitable as pharmaceutical active ingredients for mammals, especially for humans, in the treatment of tyrosine kinase-induced diseases. These diseases include the proliferation of tumour cells, pathological neovascularisation (or angiogenesis) which promotes the growth of solid tumours, ocular neovascularisation (diabetic retinopathy, age-related macular degeneration and the like) and inflammation (psoriasis, rheumatoid arthritis and the like).

The present invention encompasses the use of compounds of the formula I and/or physiologically acceptable salts and solvates thereof for the preparation of a medicament for the treatment or prevention of cancer. Preferred carcinomas for the treatment originate from the group consisting of cerebral carcinoma, urogenital tract carcinoma, carcinoma of the lymphatic system, stomach carcinoma, laryngeal carcinoma and lung carcinoma. A further group of preferred forms of cancer are monocytic leukaemia, lung adenocarcinoma, small cell lung carcinomas, pancreatic cancer, glioblastomas and breast carcinoma.

Also encompassed is the use of compounds of the formula I and/or physiologically acceptable salts and solvates thereof for the preparation of a medicament for the treatment or prevention of a disease in which angiogenesis is implicated. Such a disease in which angiogenesis is implicated is an ocular disease, such as retinal vascularisation, diabetic retinopathy, age-related macular degeneration and the like.

The use of compounds of the formula I and/or physiologically acceptable salts and solvates thereof for the preparation of a medicament for the treatment or prevention of inflammatory diseases also falls within the scope of the present invention. Examples of such inflammatory diseases include rheumatoid arthritis, psoriasis, contact dermatitis, delayed hypersensitivity reactions and the like.

Also encompassed is the use of compounds of the formula I and/or physiologically acceptable salts and solvates thereof for the preparation of a medicament for the treatment or prevention of a tyrosine kinase-induced disease or a tyrosine kinase-induced condition in a mammal, in which a therapeutically effective amount of a compound of the formula I is administered to a sick mammal in need of such treatment. The therapeutic amount varies according to the specific disease and can be determined by the person skilled in the art without undue effort.

The present invention also encompasses the use of compounds of the formula I and/or physiologically acceptable salts and solvates thereof for the preparation of a medicament for the treatment or prevention of retinal vascularisation.

Methods for the treatment or prevention of ocular diseases, such as diabetic retinopathy and age-related macular degeneration, are likewise part of the invention. The use for the treatment or prevention of inflammatory diseases, such as rheumatoid arthritis, psoriasis, contact dermatitis and delayed hypersensitivity reactions, as well as the treatment or prevention of bone pathologies from the group consisting of osteosarcoma, osteoarthritis and rickets, likewise falls within the scope of the present invention. The term "tyrosine kinase-induced diseases or conditions" refers to pathological conditions that depend on the activity of one or more tyrosine kinases. Tyrosine kinases either directly or indirectly participate in the signal transduction pathways of a variety of cellular activities, including proliferation, adhesion and migration and differentiation. Diseases associated with tyrosine kinase activity include proliferation of tumour cells, pathological neovascularisation that promotes the growth of solid tumours, ocular neovascularisation (diabetic retinopathy, age-related macular degeneration and the like) and inflammation (psoriasis, rheumatoid arthritis and the like).

The compounds of the formula I or salts or solvents thereof can be administered to patients for the treatment of cancer. The present compounds inhibit tumour angiogenesis, thereby affecting the growth of tumours (J. Rak et al. *Cancer Research*, 55:4575-4580, 1995). The angiogenesis-inhibiting properties of the present compounds of the formula I or salts or solvates thereof are also suitable for the treatment of certain forms of blindness related to retinal neovascularisation.

The compounds of the formula I or salts or solvates thereof are also suitable for the treatment of certain bone pathologies, such as osteosarcoma, osteoarthritis and rickets, also known as oncogenic osteomalacia (Hasegawa et al., Skeletal Radiol. 28, pp.4145, 1999; Gerber et al., Nature Medicine, Vol. 5, No. 6, pp.623-628, June 1999). Since VEGF directly promotes osteoclastic bone resorption through KDR/Flk-1 expressed in mature osteoclasts (FEBS Let. 473:161-164 (2000); Endocrinology, 141:1667 (2000)), the present compounds are also suitable for the treatment and prevention of conditions related to bone resorption, such as osteoporosis and Paget's disease.

The compounds can also be used for the reduction or prevention of tissue damage which occurs after cerebral ischaemic events, such as strokes, by reducing cerebral oedema, tissue damage and reperfusion injury following ischaemia (*Drug News Perspect* 11:265-270 (1998); *J. Clin. Invest.* 104:1613-1620 (1999)).

The compounds of the formula I or salts or solvates thereof are suitable for the preparation of a medicament for the treatment of diseases which are caused, mediated and/or propagated by Raf kinases, where the Raf kinase is selected from the group consisting of A-Raf, B-Raf and Raf-1. Preference is given to the use for the treatment of diseases, preferably from the group consisting of hyperproliferative and non-hyperproliferative diseases. These are cancerous diseases or non-cancerous diseases. The non-cancerous diseases are selected from the group consisting of psoriasis, arthritis, inflammation, endometriosis, scarring, benign prostatic hyperplasia, immunological diseases, autoimmune diseases and immunodeficiency diseases.

The cancerous diseases are selected from the group consisting of brain cancer, lung cancer, squamous cell cancer, bladder cancer, gastric cancer, pancreatic cancer, hepatic cancer, renal cancer, colorectal cancer, breast cancer, head cancer, neck cancer, oesophageal cancer, gynaecological cancer, thyroid cancer, lymphoma, chronic leukaemia and acute leukaemia.

The compounds according to the invention can be administered to mammals, preferably humans, either alone or preferably in combination with pharmaceutically acceptable excipients or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration. On oral use of a chemotherapeutic compound according to the invention, the selected compound can be administered, for example, in the form of tablets or capsules or as an aqueous solution or suspension. In the case of tablets for oral use, the excipients usually used include lactose and corn starch, and lubricants, such as magnesium stearate, are usually added. On oral administration in capsule form, suitable diluents include lactose and dried corn starch. If aqueous suspensions are required for oral use, the active ingredient is combined with emulsifiers and suspending agents. If desired, certain sweetening and/or flavouring agents can be added. On intramuscular, intraperitoneal, subcutaneous and intravenous use, sterile solutions of the active ingredient are usually prepared, and the pH of the solutions should be adjusted and buffered in a suitable manner. For intravenous use, the total concentration of solutes should be set so that the preparation becomes isotonic. However, the specific dose for the particular patient depends on a number of factors, for example on the efficacy of the particular compounds used, on the age, body weight, general state of health, sex, on the diet, on the time and method of administration, on the excretion rate, the type of administration, the medicament form to be administered, the medicament combination and the severity of the disease against which the therapy is employed. The particular therapeutically effective dose for the particular patient can readily be determined by routine experiments, for example by the doctor advising or attending this therapeutic treatment.

The substances according to the invention are generally preferably administered in doses of between about 1 and 500 mg, in particular between 5 and 100 mg per dosage unit. The daily dose is preferably between about 0.02 and 10 mg/kg of body weight.

The compounds according to the invention may also be administered at the same time as other well-known therapeutic agents that are selected for their particular usefulness against the condition that is being treated. For example, in the case of bone conditions, combinations that would be favourable include those with antiresorptive bisphosphonates, such as alendronate and risedronate; integrin blockers (as defined further below), such as αvβ3 antagonists; conjugated oestrogens used in hormone replacement therapy, such as Prempro®, Premarin® and Endometrion®; selective oestrogen receptor modulators (SERMs), such as raloxifene, droloxifene, CP-336,156 (Pfizer) and lasofoxifene; cathepsin K inhibitors; and ATP proton pump inhibitors.

The present compounds are also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-COA reductase inhibitors, HIV protease inhibitors, reverse transcriptase inhibitors and other angiogenesis inhibitors. The present compounds are particularly suitable for administration at the same time as radiotherapy. The synergistic effects of inhibiting VEGF in combination with radiotherapy have been described in the art (see WO 00/61186).

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl-2,2-dimethylpropanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenyl retinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors. Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)-bis-mu-(hexane-1,6-diamine)-mu-[diamine-platinum(II)]bis[diamine(chloro)platinum(II)] tetrachloride, diarizidinyl-spermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755 and 4-demethoxy-3-deamino-3-aziridinyl-4-methylsulfonyldaunorubicin (see WO 00/50032). Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797. Some examples of topoisomerase inhibitors are topotecan, hycaptamine, irinotecan, rubitecan, 6-ethoxypropionyl-3',4'-O-exobenzylidene-chartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H, 12H-benzo[de]pyrano[3',4':b,7]indolizino[1,2b]quinoline-10,13(9H, 15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa, 9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxy-benzo[c]phenanthridinium, 6,9-bis[(2-aminoethyl)amino]benzo[g]isoquinoline-5, 10-dione, 5-(3-aminopropylamino)-7, 10-dihydroxy-2-(2-hydroxyethylaminomethyl)-6H-pyrazolo[4,5,1-de]acridin-6-one, N-[1-[2-(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]-amino]-3-hydroxy-7H-indeno[2,1-c]quinolin-7-one and dimesna. "Antiproliferative agents" include antisense RNA and DNA oligonucleotides such as G3139, ODN698, RVASKRAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-d ichlorophenyl)urea, N6-[4-deoxy-4-[N2-[2(E),4(E)-tetradecadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimid ino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo(7.4.1.0.0)tetradeca-2, 4,6-trien-9-ylacetic acid ester, swainsonine, lometrexol, dexrazoxane, methioninase, 2'-cyano-2'-deoxy-N-4-palmitoyl-1-B-D-arabinofuranosyl cytosine and 3-aminopyridine-2-carboxaldehyde thiosemicarbazone. "Antiproliferative agents" also include monoclonal antibodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

The invention furthermore relates to the use of compounds of the formula I and/or physiologically acceptable salts and solvates thereof for the preparation of a medicament for the treatment of diseases and/or dysfunctions which are characterised by oxidative stress conditions in a mammal in need of such treatment, in which a therapeutically effective amount of a compound of formula I is administered orally to the mammal in need of such treatment.

The diseases and/or dysfunctions are, in particular, memory loss and neurodegenerative diseases.

The compounds according to the invention are therefore used for neuroprotection.

The use of isoquercetin and ascorbic acid for corresponding purposes is described in WO 00/54754.

The invention furthermore relates to the use of the compounds according to the invention and/or physiologically acceptable salts and solvates thereof as food supplements.

The invention furthermore relates to a composition comprising ascorbic acid, ascorbate or an ascorbic acid derivative and at least one compound according to the invention and/or a physiologically acceptable salt or solvate thereof.

As flavonoid derivatives, the compounds according to the invention and salts and solvates thereof have antioxidative properties.

The use of ectoin derivatives with antioxidants for the protection of stress proteins of the skin in topical formulations is described, for example, in WO 01/72263.

The invention therefore relates to the use of the compounds according to the invention and/or physiologically acceptable salts and solvates thereof in cosmetic formulations, preferably in the form of a topical formulation.

The invention furthermore relates to the use of the compounds according to the invention and/or physiologically acceptable salts and solvates thereof for protection of the stress proteins of the skin, preferably in the form of a topical formulation.

The topical composition is prepared by converting at least one of the compounds used in accordance with the invention into a suitable formulation form, if desired with adjuvants and/or excipients. The adjuvants and excipients originate from the group consisting of the vehicles, preservatives and other conventional adjuvants.

The topical compositions based on at least one compound used in accordance with the invention are applied externally to the skin or the skin adnexa.

Examples of application forms which may be mentioned are solutions, suspensions, emulsions, pastes, ointments, gels, creams, lotions, powders, soaps, surfactant-containing cleansing preparations, oils and sprays. In addition to one or more compounds used in accordance with the invention, any desired conventional excipients, adjuvants and, if desired, further active ingredients are added to the composition.

Preferred adjuvants originate from the group consisting of preservatives, antioxidants, stabilisers, solubilisers, vitamins, colorants and odour improvers. Besides one or more compounds used in accordance with the invention, ointments, pastes, creams and gels may comprise the conventional excipients, for example animal and vegetable fats, waxes, paraffins, starch, tragacanth, cellulose derivatives, polyethylene glycols, silicones, bentonites, silica, talc and zinc oxide, or mixtures of these substances.

Besides one or more compounds used in accordance with the invention, powders and sprays may comprise the conventional excipients, for example lactose, talc, silica, aluminium hydroxide, calcium silicate and polyamide powder, or mixtures of these substances. Sprays may additionally comprise the conventional propellants, for example chlorofluorocarbons, propane/butane or dimethyl ether.

Besides one or more compounds used in accordance with the invention, solutions and emulsions may comprise the conventional excipients, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oils, peanut oil, wheatgerm oil, olive oil, castor oil and sesame oil, glycerol fatty acid esters, polyethylene glycols and fatty acid esters of sorbitan, or mixtures of these substances.

Besides one or more compounds used in accordance with the invention, suspensions may comprise the conventional excipients, such as liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Besides one or more compounds used in accordance with the invention, soaps may comprise the conventional excipients, such as alkali metal salts of fatty acids, salts of fatty acid monoesters, fatty acid protein hydrolysates, isethionates, lanolin, fatty alcohol, vegetable oils, plant extracts, glycerol, sugars, or mixtures of these substances.

Besides one or more compounds used in accordance with the invention, surfactant-containing cleansing products may comprise the conventional excipients, such as salts of fatty alcohol sulfates, fatty alcohol ether sulfates, sulfosuccinic acid monoesters, fatty acid protein hydrolysates, isethionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Besides one or more compounds used in accordance with the invention, face and body oils may comprise the conventional excipients, such as synthetic oils, such as fatty acid esters, fatty alcohols, silicone oils, natural oils, such as vegetable oils and oily plant extracts, paraffin oils, lanolin oils, or mixtures of these substances.

Further typical cosmetic application forms are also lipsticks, lip-care sticks, mascara, eyeliner, eye shadow, rouge, powder make-up, emulsion make-up and wax make-up and sunscreen, pre-sun and after-sun preparations.

At least one compound used in accordance with the invention is present in the topical composition in an amount of preferably from 0.0001 to 50% by weight, particularly preferably from 0.001 to 10% by weight, especially preferably from 0.1 to 1% by weight, based on the composition.

Assays

The compounds according to the invention described in the examples were tested by the assays described below and were found to have kinase inhibitory activity. Other assays are known from the literature and could readily be performed by the person skilled in the art (see, for example, Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., *In Vitro* 18:538-549).

VEGF Receptor Kinase Assay

VEGF receptor kinase activity is measured by incorporation of radio-labelled phosphate into 4:1 polyglutamic acid/tyrosine substrate (pEY). The phosphorylated pEY product is trapped onto a filter membrane and the incorporation of radiolabelled phosphate is quantified by scintillation counting.

Materials

VEGF Receptor Kinase

The intracellular tyrosine kinase domains of human KDR (Terman, B. I. et al. Oncogene (1991) Vol. 6, pp. 1677-1683.) and Flt-1 (Shibuya, M. et al. Oncogene (1990) Vol. 5, pp. 519-524) were cloned as glutathione S-transferase (GST) gene fusion proteins. This was accomplished by cloning the cytoplasmic domain of the KDR kinase as an in frame fusion at the carboxyl terminus of the GST gene. Soluble recombinant GST-kinase domain fusion proteins were expressed in *Spodoptera frugiperda* (Sf21) insect cells (Invitrogen) using a baculovirus expression vector (pAcG2T, Pharmingen).

Lysis Buffer 50 mM Tris pH 7.4, 0.5 M NaCl, 5 mM DTT, 1 mM EDTA, 0.5% triton X-100, 10% glycerol, 10 mg/ml each of leupeptin, pepstatin and aprotinin and 1 mM phenylmethylsulfonyl fluoride (all Sigma).

Wash Buffer 50 mM Tris pH 7.4, 0.5 M NaCl, 5 mM DTT, 1 mM EDTA, 0.05% triton X-100, 10% glycerol, 10 mg/ml each of leupeptin, pepstatin and aprotinin and 1 mM phenylmethylsulfonyl fluoride.

Dialysis Buffer 50 mM Tris pH 7.4, 0.5 M NaCl, 5 mM DTT, 1 mM EDTA, 0.05% triton X-100, 50% glycerol, 10 mg/ml each of leupeptin, pepstatin and aprotinin and 1 mM phenylmethylsulfonyl fluoride.

10× Reaction Buffer 200 mM Tris, pH 7.4, 1.0 M NaCl, 50 mM $MnCl_2$, 10 mM DTT and 5 mg/ml bovine serum albumin [BSA] (Sigma).

Enzyme Dilution Buffer 50 mM Tris, pH 7.4, 0.1 M NaCl, 1 mM DTT, 10% glycerol, 100 mg/ml BSA.

10× Substrate

750 μg/ml poly(glutamic acid/tyrosine; 4:1) (Sigma).

Stop Solution

30% trichloroacetic acid, 0.2 M sodium pyrophosphate (both Fisher).

Wash Solution

15% trichloroacetic acid, 0.2 M sodium pyrophosphate.

Filter Plates

Millipore #MAFC NOB, GF/C glass fibre 96 well plate.

Method A—Protein Purification

1. Sf21 cells were infected with recombinant virus at a multiplicity of infection of 5 virus particles/cell and grown at 27° C. for 48 hours.

2. All steps were performed at 4° C. Infected cells were harvested by centrifugation at 1000×g and lysed at 4° C. for 30 minutes with 1/10 volume of lysis buffer followed by centrifugation at 100,000×g for 1 hour. The supernatant was then passed over a glutathione Sepharose column (Pharmacia) equilibrated with lysis buffer and washed with 5 volumes of the same buffer followed by 5 volumes of wash buffer. Recombinant GST-KDR protein was eluted with wash buffer/10 mM reduced glutathione (Sigma) and dialysed against dialysis buffer.

Method B—VEGF Receptor Kinase Assay

1. Add 5 μl of inhibitor or control to the assay in 50% DMSO.
2. Add 35 μl of reaction mixture containing 5 μl of 10× reaction buffer, 5 μl of 25 mM ATP/10 μCi[$^{33}$P]ATP (Amersham) and 5 μl of 10× substrate.
3. Start the reaction by the addition of 10 μl of KDR (25 nM) in enzyme dilution buffer.
4. Mix and incubate at room temperature for 15 minutes.
5. Stop the reaction by the addition of 50 μl of stop solution.
6. Incubate for 15 minutes at 4° C.
7. Transfer a 90 μl aliquot to filter plate.
8. Aspirate and wash 3 times with wash solution.
9. Add 30 μl of scintillation cocktail, seal plate and count in a Wallace Microbeta scintillation counter.

Human Umbilical Vein Endothelial Cell Mitogenesis Assay

Expression of VEGF receptors that mediate mitogenic responses to the growth factor is largely restricted to vascular endothelial cells. Human umbilical vein endothelial cells (HUVECs) in culture proliferate in response to VEGF treatment and can be used as an assay system to quantify the effects of KDR kinase inhibitors on VEGF stimulation. In the assay described, quiescent HUVEC monolayers are treated with vehicle or test compound 2 hours prior to addition of VEGF or basic fibroblast growth factor (bFGF). The mitogenic response to VEGF or bFGF is determined by measuring the incorporation of [$^3$H]thymidine into cellular DNA.

Materials

HUVECs

HUVECs frozen as primary culture isolates are obtained from Clonetics Corp. Cells are maintained in endothelial growth medium (EGM; Clonetics) and are used for mitogenic assays at passages 3-7.

Culture Plates

NUNCLON 96-well polystyrene tissue culture plates (NUNC #167008).

Assay Medium

Dulbecco's modification of Eagle's medium containing 1 g/ml glucose (low-glucose DMEM; Mediatech) plus 10% (v/v) foetal bovine serum (Clonetics).

Test Compounds

Working stock solutions of test compounds are diluted serially in 100% dimethyl sulfoxide (DMSO) to 400 times greater than their desired final concentrations. Final dilutions to 1× concentration are made into assay medium immediately prior to addition to cells.

10× Growth Factors

Solutions of human VEGF 165 (500 ng/ml; R&D Systems) and bFGF (10 ng/ml; R&D Systems) are prepared in assay medium.

10×[³H]thymidine

[Methyl-3H]thymidine (20 Ci/mmol; Dupont-NEN) is diluted to 80 µCi/ml in low-glucose DMEM.

Cell Wash Medium

Hank's balanced salt solution (Mediatech) containing 1 mg/ml bovine serum albumin (Boehringer-Mannheim).

Cell Lysis Solution

1 N NaOH, 2% (w/v) $Na_2CO_3$.

Method 1

HUVEC monolayers maintained in EGM are harvested by trypsinisation and plated out at a density of 4000 cells per 100 µl of assay medium per well in 96-well plates. Cell growth is arrested for 24 hours at 37° C. in a humidified atmosphere containing 5% $CO_2$.

Method 2

Growth-arrest medium is replaced by 100 µl of assay medium containing either vehicle (0.25% [v/v] DMSO) or the desired final concentration of test compound. All determinations are performed in triplicate. Cells are then incubated at 37° C./5% $CO_2$ for 2 hours to allow test compounds to enter cells.

Method 3

After the 2-hour pre-treatment period, cells are stimulated by addition of 10 µl/well of either assay medium, 10×VEGF solution or 10×bFGF solution. Cells are then incubated at 37° C./5% $CO_2$.

Method 4

After 24 hours in the presence of growth factors, 10× [³H]thymidine (10 µl/well) is added.

Method 5

Three days after addition of [³H]thymidine, medium is removed by aspiration, and cells are washed twice with cell wash medium (400 µl/well followed by 200 µl/well). The washed, adherent cells are then solubilised by addition of cell lysis solution (100 µl/well) and warming to 37° C. for 30 minutes. Cell lysates are transferred to 7 ml glass scintillation vials containing 150 µl of water. Scintillation cocktail (5 ml/vial) is added, and cell-associated radioactivity is determined by liquid scintillation spectroscopy. According to these assays, the compounds of the formula I are inhibitors of VEGF and are thus suitable for the inhibition of angiogenesis, such as in the treatment of ocular diseases, for example diabetic retinopathy, and for the treatment of carcinomas, for example solid tumours. The present compounds inhibit VEGF-stimulated mitogenesis of human vascular endothelial cells in culture with IC50 values of 0.01-5.0 µM. These compounds also show selectivity over related tyrosine kinases (for example FGFR[1] and the Src family; for relationship between Src kinases and VEGFR kinases, see Eliceiri et al., Molecular Cell, Vol. 4, pp.915-924, December 1999).

Test for Investigating the Free-Radical Scavenger Properties or Antioxidative Action The assay serves for screening the antioxidative or free-radical scavenger property of a substance or extract. In order to determine this property, the substance is allowed to react with the stable free radical DPPH* (2,2-diphenyl-1-picryl-hydrazyl hydrate) in ethanol solution. The reduction of DPPH* is followed via the drop in absorbance at the characteristic wavelength of the free radical. In its free-radical form, DPPH* absorbs at 515 nm, while on reduction by an antioxidant (AOX), the absorbance drops. Different concentrations are investigated for each antioxidant (expressed as the ratio of mol of antioxidant/mol of DPPH*). The drop in absorbance at 515 nm is determined after 1 second, 2 minutes, 10 minutes and then every 10 minutes until the absorbance remains constant. The precise initial concentration of DPPH* is determined with the aid of the absorption coefficient. At each antioxidant concentration, the remaining DPPH* concentration is determined as percent of the starting concentration and plotted against the molar ratio of antioxidant with DPPH*. The anti-free-radical activity is defined as the proportion of antioxidant which lowers the DPPH concentration to 50 percent of the initial amount (efficient concentration=$EC_{50}$). The smaller this value, the greater the activity against free radicals. The reaction behaviour of the individual antioxidants varies greatly. A distinction can be drawn between fast-, medium- and slow-reacting substances, with the steady state being reached between 30 seconds and 12 hours.

Above and below, all temperatures are indicated in ° C. and, all parts and percentages are by weight, unless otherwise indicated. In the following examples, "conventional work-up" means that, if necessary, water is added, the pH is adjusted, if necessary, to a value of between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS): EI (electron impact ionisation) $M^+$

FAB (fast atom bombardment) $(M+H)^+$

ESI (electrospray ionisation) $(M+H)^+$ (unless stated otherwise).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

EXAMPLE 1

Preparation of 6-hydroxy-2-(1-methyl-1H-imidazole-2-carbonyl)chromen-4-one 1.1 3.8 g of sodium are dissolved in portions in 300 ml of ethanol with stirring. A solution of 5.0 g of 2,5-dihydroxy-acetophenone and 17.8 ml of diethyl oxalate in 25 ml of ethanol is subsequently added dropwise. The reaction mixture is then heated at 800 for 3 hours and cooled to room temperature, and 10 ml of 32% HCl are added dropwise. The mixture is heated at 90° for 30 minutes and cooled, and the solvent is removed. Conventional work-up gives 5.6 g of 6-hydroxy-2-ethoxycarbonylchromen-4-one ("AA").

1.2 2.4 ml of 1.6 M n-BuLi solution are added to a solution, cooled to −78°, of 0.3 ml of 1-methyl-1H-imidazole in 5 ml of THF under an $N_2$ atmosphere, and the mixture is stirred for a further 30 minutes. A solution of 300 mg of "AA" in 5 ml of THF is subsequently added, and the mixture is stirred for a further 1 hour. Conventional work-up gives 303 mg of 6-hydroxy-2-(1-methyl-1 H-imidazole-2-carbonyl)chromen-4-one.

¹H NMR (DMSO-d6) δ 4.02 (s, 3H), 7.32 (m, 3H), 7.59 (s, 1H), 7.62 (dd, J=9.6, 2.0 Hz, 1H), 7.74 (s, 1H), 10.21(s, 1H).

$^{13}$C NMR (DMSO-d6) δ 36.1, 107.2, 115.3, 120.3, 124.2, 124.6, 129.7, 129.9, 141.1, 149.2, 155.2, 156.0, 174.8, 177.4.

EI MS (m/e) 267 (M$^+$), 239, 211

UV-Vis ($^i$PrOH): λ$_{max}$. (lg. ε):

The following compounds are obtained analogously:

6-hydroxy-2-(1-methyl-1H-imidazolee-2-carbonyl) chromen-4-one, 5,7-dihydroxy-2-(1-methyl-1H-imidazole-2-carbonyl)chromen-4-one, 7-hydroxy-2-(1-methyl-1H-imidazole-2-carbonyl) chromen-4-one, 6-(11-methyl-1H-imidazole-2-carbonyl)-1,3-dioxolo[4,5 g]chromen-8-one, 5,7-dihydroxy-2-(pyridine-2-carbonyl)chromen-4-one,
6-hydroxy-2-(pyridine-2-carbonyl)chromen-4-one,
6-hydroxy-2-(3,5-dichloropyrazine-2-carbonyl) chromen-4-one, 6-hydroxy-2-(benzothiazolyl-2-carbonyl)chromen-4-one.

| Pharmacological test results | | | |
|---|---|---|---|
| Structure | Inhibition of PKB IC$_{50}$ (μmol) | Inhibition of RAF IC$_{50}$ (μmol) | Inhibition of Tie2 IC$_{50}$ (μmol) |
| 6-hydroxy-2-(3,5-dichloropyrazine-2-carbonyl)chromen-4-one | 9.4 | >1.0 | >10 |
| 5,7-dihydroxy-2-(1-methyl-1H-imidazole-2-carbonyl)chromen-4-one | >10 | >1.0 | >10 |
| 6-hydroxy-2-(1-methyl-1H-imidazole-2-carbonyl)chromen-4-one | >10 | >1.0 | >10 |
| 5,7-dihydroxy-2-(pyridine-2-carbonyl)chromen-4-one | >10 | >1.0 | >10 |
| 6-hydroxy-2-(pyridine-2-carbonyl)chromen-4-one | >10 | >1.0 | >10 |
| 6-hydroxy-2-(benzothiazolyl-2-carbonyl)chromen-4-one | >10 | >1.0 | >10 |

The following examples relate to pharmaceutical preparations:

EXAMPLE A

Injection Vials

A solution of 100 g of an active ingredient of the formula I and 5 g of disodium hydrogenphosphate in 3 l of bidistilled water is adjusted to pH 6.5 using 2N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Coated Tablets

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The entire disclosures of all applications, patents and publications, cited herein and of corresponding German application No. 10319552.1, filed Apr. 30, 2003, and German application No. 10335782.3 filed Aug. 5, 2003 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula I

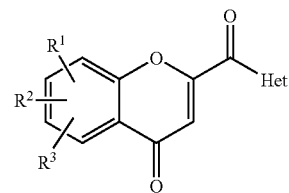

wherein
$R^1$ is —OH, or —OA,
$R^2$ is H, —OH, —OA, phenoxy, —O—CO-A, —OSO$_3$H, —OSO$_3$A, —OSO$_2$A, or Hal,
$R^3$ is H,
$R^1$ and $R^2$ together are alternatively methylenedioxy or ethylenedioxy,
Het is chromen-2-onyl, benzothiazolyl, thienyl, pyridinyl, pyrimidinyl, pyrazinyl, indolyl, furyl, pyrrolyl, isoxazolyl, imidazolyl, thiazolyl, triazilyl, tetrazolyl, quinolyl or isoquinolyl, each of which is unsubstituted or mono- or disubstituted by Hal and/or A, and
A is unbranched or branched alkyl having 1-6 carbon atoms, where 1-5 H atoms may be replaced by F, or
a salt thereof.

2. A compound according to claim 1, wherein
$R^1$ is —OH, or —OA,
$R^2$ is H, —OH, —OA, Hal,
$R^3$ is H,
$R^1$ and $R^2$ together are alternatively methylenedioxy or ethylenedioxy,
Het is benzothiazolyl, pyridinyl, pyrimidinyl, pyrazinyl, indolyl, furyl, pyrrolyl, isoxazolyl, imidazolyl or thiazolyl, each of which is unsubstituted or mono- or disubstituted by Hal and/or A, and
A is unbranched or branched alkyl having 1-6 carbon atoms, where 1-5 H atoms may be replaced by F.

3. A compound according to claim 1, wherein the compound of formula I is present in the form of stereoisomers of said compound.

4. A compound according to claim 1, wherein the compound of formula I is present in the form of a mixture of isomers.

5. A compound, which is 6-hydroxy-2-(1-methyl-1H-imidazole-2-carbonyl) chromen-4-one, 5,7-dihydroxy-2-(1-methyl-1H-imidazole-2-carbonyl)chromen-4-one, 7-hydroxy-2-(1-methyl-1H-imidazole-2-carbonyl)chromen-4-one, 6-(1-methyl-1H-imidazole-2-carbonyl)-1,3-dioxolo[4,5g] chromen-8-one, 5,7-dihydroxy-2-(pyridine-2-carbonyl)chromen-4-one, 6-hydroxy-2-(pyridine-2-carbonyl)chromen-4-one, 6-hydroxy-2-(3,5-dichloropyrazine-2-carbonyl)chromen-4-one, or 6-hydroxy-2-(benzothiazolyl-2-carbonyl)chromen-4-one or a salt thereof.

6. A pharmaceutical composition comprising a therapeutically effective amount of a compound according to claim 1 and a pharmaceutically acceptable carrier.

7. A cosmetic composition comprising a compound according to claim 1, and a cosmetically acceptable carrier.

8. A process for preparing a compound according to claim 1, comprising a) reacting a compound of formula II

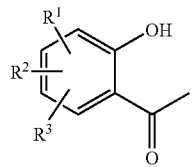

in which
$R^1$ is —OH, or —OA,
$R^2$ is H, —OH, —OA, phenoxy, —O—CO-A, —OSO$_3$H, —OSO$_3$A, —OSO$_2$A, or Hal,
$R^3$ is H,
with a compound of formula III

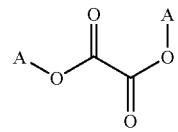

in which
A is alkyl having 1,2,3,4, 5 or 6 carbon atoms, to give a compound of formula IV

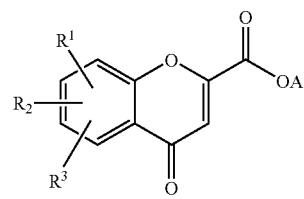

in which $A^1$, $R^1$, $R^2$ and $R^3$ are as defined above, b) then reacting the compound of formula IV with a compound of formula V M-Het  V in which
Het is chromen-2-onyl, benzothiazolyl, thienyl, pyridinyl, pyrimidinyl, pyrazinyl, indolyl, furyl, pyrrolyl, isoxazolyl, imidazolyl, thiazolyl, triazolyl, tetrazolyl, quinolyl or isoquinolyl, each of which is unsubstituted or mono- or disubstituted by Hal and/or A,
M is sodium, potassium or lithium,
to give a compound of the formula I,
and optionally
c) a base or acid of formula I is converted into one of its salts.

* * * * *

UNITED STATES PATENT AND TRADEMARK OFFICE
CERTIFICATE OF CORRECTION

PATENT NO. : 7,378,421 B2 Page 1 of 1
APPLICATION NO. : 10/833159
DATED : May 27, 2008
INVENTOR(S) : Teresa Mujica-Fernaud It is certified that error appears in the above-identified patent and that said Letters Patent is hereby corrected as shown below:

Column 34, line 47, reads "triazilyl" should read --triazolyl--
Column 36, line 36, reads "to give a compound of the formula I," should read --to give a compound of formula I--

Signed and Sealed this

Sixteenth Day of December, 2008

JON W. DUDAS
*Director of the United States Patent and Trademark Office*